US012672947B2

(12) United States Patent
Ruefer et al.

(10) Patent No.: US 12,672,947 B2
(45) Date of Patent: Jul. 7, 2026

(54) PROSTHETIC SURGICAL SLING

(71) Applicants: Rebecca U. Ruefer, Bozeman, MT (US); Beda B. G. Ruefer, Bozeman, MT (US)

(72) Inventors: Rebecca U. Ruefer, Bozeman, MT (US); Beda B. G. Ruefer, Bozeman, MT (US)

( * ) Notice: Subject to any disclaimer, the term of this patent is extended or adjusted under 35 U.S.C. 154(b) by 1056 days.

(21) Appl. No.: 17/580,434

(22) Filed: Jan. 20, 2022

(65) Prior Publication Data

US 2022/0226093 A1 Jul. 21, 2022

Related U.S. Application Data

(60) Provisional application No. 63/140,052, filed on Jan. 21, 2021.

(51) Int. Cl.
B29D 7/01 (2006.01)
A61F 2/00 (2006.01)
(Continued)

(52) U.S. Cl.
CPC .......... A61F 2/0036 (2013.01); A61F 2/0045 (2013.01); A61L 31/048 (2013.01); A61L 31/06 (2013.01); A61L 31/146 (2013.01); A61L 31/16 (2013.01); B29C 48/0018 (2019.02); B29C 48/09 (2019.02); B29D 7/01 (2013.01); A61F 2002/0081 (2013.01); A61F 2240/001 (2013.01); A61F 2240/002 (2013.01);
(Continued)

(58) Field of Classification Search
CPC .................. A61F 2/0036; A61F 2/0045; A61F 2002/0081; A61F 2240/001; A61F 2240/002; A61F 2002/009; A61L 31/048; A61L 31/06; A61L 31/146; A61L 31/16; A61L 2300/406; A61L 31/14; B29C 48/0018; B29C 48/09; B29D 7/01; B29K 2027/18; B29L 2031/7532
See application file for complete search history.

(56) References Cited

U.S. PATENT DOCUMENTS 3,953,566 A * 4/1976 Gore ...................... H01B 3/445
264/289.3
4,902,423 A * 2/1990 Bacino .................. B29C 55/005
210/507

(Continued)

FOREIGN PATENT DOCUMENTS

CA 2864711 C 9/2013
CN 119604254 A * 3/2025 ........... A61F 2/0063
(Continued)

OTHER PUBLICATIONS

PCT Patent Application PCT/US2023/021601 International Search Report and Written Opinion dated Aug. 11, 2023.
(Continued)

*Primary Examiner* — Brian L Casler
(74) *Attorney, Agent, or Firm* — Avek IP, LLC

(57) ABSTRACT

Disclosed is a process of making an expanded fluoropolymer, e.g., PTFE, article is disclosed. The article is formed from a PTFE resin, calendered, and then expanded (e.g., uniaxially, multiaxially, etc.) at an elevated temperature. After cooling, the article is used to form a surgically implanted device, e.g., a surgical prosthetic sling.

15 Claims, 4 Drawing Sheets

(51) Int. Cl.

| | |
|---|---|
| *A61L 31/04* | (2006.01) |
| *A61L 31/06* | (2006.01) |
| *A61L 31/14* | (2006.01) |
| *A61L 31/16* | (2006.01) |
| *B29C 48/00* | (2019.01) |
| *B29C 48/09* | (2019.01) |
| *B29C 43/24* | (2006.01) |
| *B29K 27/18* | (2006.01) |
| *B29L 31/00* | (2006.01) |

(52) U.S. Cl.

CPC ......... *A61L 2300/406* (2013.01); *B29C 43/24* (2013.01); *B29K 2027/18* (2013.01); *B29L 2031/7532* (2013.01)

(56) References Cited

U.S. PATENT DOCUMENTS

| | | | | |
|---|---|---|---|---|
| 5,112,344 | A | 5/1992 | Petros | |
| 5,433,909 | A * | 7/1995 | Martakos ........... | B01D 67/0027 |
| | | | | 264/289.3 |
| 5,476,589 | A | 12/1995 | Bacino | |
| 5,899,909 | A | 5/1999 | Claren et al. | |
| 5,934,283 | A * | 8/1999 | Willem ................. | A61F 2/0045 |
| | | | | 128/885 |
| 6,099,791 | A | 8/2000 | Shannon et al. | |
| 6,273,852 | B1 | 8/2001 | Lehe et al. | |
| 6,712,919 | B2 | 3/2004 | Ruefer et al. | |
| 6,953,428 | B2 * | 10/2005 | Gellman ............... | A61F 2/0063 |
| | | | | 600/29 |
| 7,070,558 | B2 | 7/2006 | Gellman et al. | |
| 8,007,430 | B2 * | 8/2011 | Browning ............. | A61F 2/0063 |
| | | | | 600/30 |
| 8,097,007 | B2 | 1/2012 | Evans et al. | |
| 8,123,817 | B2 * | 2/2012 | Intoccia ................ | A61F 2/0045 |
| | | | | 623/23.72 |
| 8,628,464 | B2 | 1/2014 | Bourne et al. | |
| 8,765,039 | B1 | 7/2014 | Ledergerber | |
| 8,845,512 | B2 * | 9/2014 | Evans .............. | A61B 17/06066 |
| | | | | 600/30 |
| 9,078,728 | B2 * | 7/2015 | Chu ................... | A61B 17/0482 |
| 12,397,139 | B1 * | 8/2025 | Sibary .................. | A61M 31/00 |
| 2002/0001705 | A1 | 1/2002 | Ruefer et al. | |
| 2002/0029011 | A1 | 3/2002 | Dyer | |
| 2003/0130670 | A1 * | 7/2003 | Anderson ........ | A61B 17/06004 |
| | | | | 606/151 |

| | | | | |
|---|---|---|---|---|
| 2005/0042250 | A1 | 2/2005 | Damien et al. | |
| 2005/0101834 | A1 * | 5/2005 | Merade ................. | A61F 2/0045 |
| | | | | 600/30 |
| 2005/0234291 | A1 * | 10/2005 | Gingras ................. | D04B 21/12 |
| | | | | 606/151 |
| 2006/0217812 | A1 * | 9/2006 | Lambrecht ..... | A61B 17/320016 |
| | | | | 623/17.16 |
| 2007/0152367 | A1 | 7/2007 | Kramer et al. | |
| 2007/0299538 | A1 | 12/2007 | Roeber | |
| 2008/0269547 | A1 * | 10/2008 | Hortenstine .......... | A61F 2/0045 |
| | | | | 128/885 |
| 2009/0216338 | A1 | 8/2009 | Gingras et al. | |
| 2011/0184228 | A1 | 7/2011 | Sherry et al. | |
| 2012/0065649 | A1 | 3/2012 | Towler | |
| 2012/0239161 | A1 | 9/2012 | Datta et al. | |
| 2013/0030243 | A1 | 1/2013 | Boden et al. | |
| 2013/0204355 | A1 * | 8/2013 | Goldmann ............ | A61L 31/088 |
| | | | | 623/1.39 |
| 2013/0231733 | A1 * | 9/2013 | Knisley ................. | A61F 2/0077 |
| | | | | 623/1.15 |
| 2014/0142368 | A1 | 5/2014 | Arnal et al. | |
| 2022/0226091 | A1 | 7/2022 | Ruefer et al. | |
| 2022/0226092 | A1 | 7/2022 | Ruefer et al. | |
| 2023/0363880 | A1 | 11/2023 | Ruefer et al. | |

FOREIGN PATENT DOCUMENTS

| | | | | |
|---|---|---|---|---|
| EP | 1214951 | A1 | 6/2002 | |
| WO | WO-9747246 | A1 * | 12/1997 | ........... A61B 17/062 |
| WO | 2011098565 | A1 | 8/2011 | |
| WO | 2022159654 | A1 | 7/2022 | |
| WO | 2023224844 | A1 | 11/2023 | |

OTHER PUBLICATIONS

Communication pursuant to Article 94(3) EPC issued May 30, 2025 in EP Application No. 22703516.9, 5 pages.

Falagas et al., "Mesh-related infections after pelvic organ prolapse repair surgery", European Journal of Obstetrics & Gynecology and Reproductive Biology, Sep. 26, 2007, vol. 134, No. 2, pp. 147-156, ISSN: 0301-2115.

Baggish MS, Karram MM, eds. Atlas of Pelvic Anatomy and Gynecology Surgery, ed 3. St. Louis: Saunders; 2011.

PCT Patent Application PCT/US2022/013233 International Search Report and Written Opinion dated Apr. 28, 2022.

PCT Patent Application PCT/US2022/013235 International Search Report and Written Opinion dated May 2, 2022.

* cited by examiner

PROSTHETIC SURGICAL SLING

CROSS-REFERENCE TO RELATED APPLICATIONS

This application claims the benefit of U.S. Provisional Application No. 63/140,052 filed Jan. 21, 2021, the entire contents of which are herein incorporated by reference.

BACKGROUND OF THE INVENTION

1. Field

The disclosed embodiments relate generally to the field of prosthetic medical devices. More specifically, the field relates to the development of prosthetic medical slings implemented for supporting internal body structures.

2. Description of the Related Art

Pubovaginal sling procedures are very prevalently used to offer support needed to stabilize a patient's urethra or bladder. The most common device used in executing such a process is an elongated flexible strip constructed of a non-absorbable polypropylene mesh material, the ends of which can be anchored elsewhere in the patient's body, and support is offered to prevent incontinence.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages will be apparent from the following detailed description of the embodiments and the accompanying drawing figures.

In embodiments, a medical support device includes an elongated body comprised of an expanded fluoropolymer. The device is used to support a body component, e.g., in embodiments, can be used as a urethral sling or for other like applications. In some embodiments, the elongated expanded fluoropolymer is expanded polytetrafluoroethylene (ePTFE). The ePTFE can, in embodiments, be formed into an elongated sheet.

In some aspects, the techniques described herein relate to a surgical implant including: an elongated body configured to support a body tissue, the elongated body including a first end and a second end, the elongated body formed of a biocompatible, bacteria-resistant fluoropolymer material, wherein the biocompatible, bacteria-resistant fluoropolymer material includes a plurality of nodes and a plurality of fibrils, the plurality of fibrils interconnecting the plurality of nodes.

In some aspects, the techniques described herein relate to a surgical implant, wherein the biocompatible, bacteria-resistant fluoropolymer material includes Polytetrafluoroethylene (PTFE).

In some aspects, the techniques described herein relate to a surgical implant, wherein the biocompatible, bacteria-resistant fluoropolymer material includes expanded PTFE (ePTFE).

In some aspects, the techniques described herein relate to a surgical implant, wherein the elongated body is substantially planar.

In some aspects, the techniques described herein relate to a surgical implant, wherein the surgical implant is substantially microporous.

In some aspects, the techniques described herein relate to a surgical implant, wherein the body is multiaxially expanded such that the plurality of fibrils radiate between the plurality of nodes to define a plurality of pores.

In some aspects, the techniques described herein relate to a surgical implant, wherein the plurality of fibrils are about 0.5 to about 3 microns in length.

In some aspects, the techniques described herein relate to a surgical implant, wherein the plurality of pores defined between the plurality of nodes and fibrils are less than or equal to 2 by 1 microns in size.

In some aspects, the techniques described herein relate to a surgical implant, wherein the elongated body is uniaxially expanded such that the plurality of fibrils extend substantially longitudinally between the plurality of nodes to define a plurality of elongated pores.

In some aspects, the techniques described herein relate to a surgical implant, wherein the plurality of fibrils are about 0.5 to about 3.0 microns in length.

In some aspects, the techniques described herein relate to a surgical implant, wherein the plurality of pores defined between the plurality of nodes and the plurality of fibrils have widths which are less than about 3 microns.

In some aspects, the techniques described herein relate to a surgical implant, wherein the elongated body has a thickness of about 0.60 mm.

In some aspects, the techniques described herein relate to a surgical implant, wherein the surgical implant is configured for use as a pubovaginal sling.

In some aspects, the techniques described herein relate to a surgical implant, wherein the first end is configured to receive a first surgical placement aid, and the second end is configured to receive a second surgical placement aid.

In some aspects, the techniques described herein relate to a surgical implant, wherein the biocompatible, bacteria-resistant fluoropolymer material includes a microporous structure which is relatively closed to ingrowth and bacterial penetration.

In some aspects, the techniques described herein relate to a method for producing a supportive surgical implant device, the method including: mixing a PTFE resin paste with an extrusion aid; configuring the PTFE resin paste and the extrusion aid into a pre-extrusion form; calendaring the pre-extrusion form to make a PTFE article; drying the extrusion aid from the PTFE article; reheating the PTFE article at a temperature higher than a drying temperature used in the drying step, but lower than a melt temperature of the PTFE article; expanding the PTFE article to create a node/fibril structure; restraining the PTFE article in an expanded state and heating the PTFE article to a temperature above a thermal transition temperature for the PTFE article to lock the node/fibril structure in place; allowing the PTFE article to cool; and configuring the PTFE article for use as the supportive surgical implant device.

In some aspects, the techniques described herein relate to a method, including: forming the PTFE article into a sheet; and causing at least a portion of the sheet to have an elongated body and two ends.

In some aspects, the techniques described herein relate to a method, including: configuring the ends of the at least a portion of the sheet to attach to one or more surgical placement aids.

In some aspects, the techniques described herein relate to a method, wherein the expanding step is a substantially unidirectional expansion resulting in a plurality of elongated fibrils, each fibril in the plurality being substantially parallel relative to the others.

In some aspects, the techniques described herein relate to a method, wherein the expanding step is a multiaxial expansion resulting in a plurality of fibrils which radiate between a plurality of nodes.

Regardless of the particular configuration involved, the elongated medical support device can have first and second ends both receivable by a placement tool designed to aid with implanting the device into the human body in a supporting capacity regarding an internal structure. In some embodiments the device is a sling.

BRIEF DESCRIPTION OF THE SEVERAL VIEWS OF THE DRAWINGS

Illustrative embodiments are described in detail below with reference to the attached drawing figures, which are incorporated by reference herein and wherein.

Figures 1A, 1B:
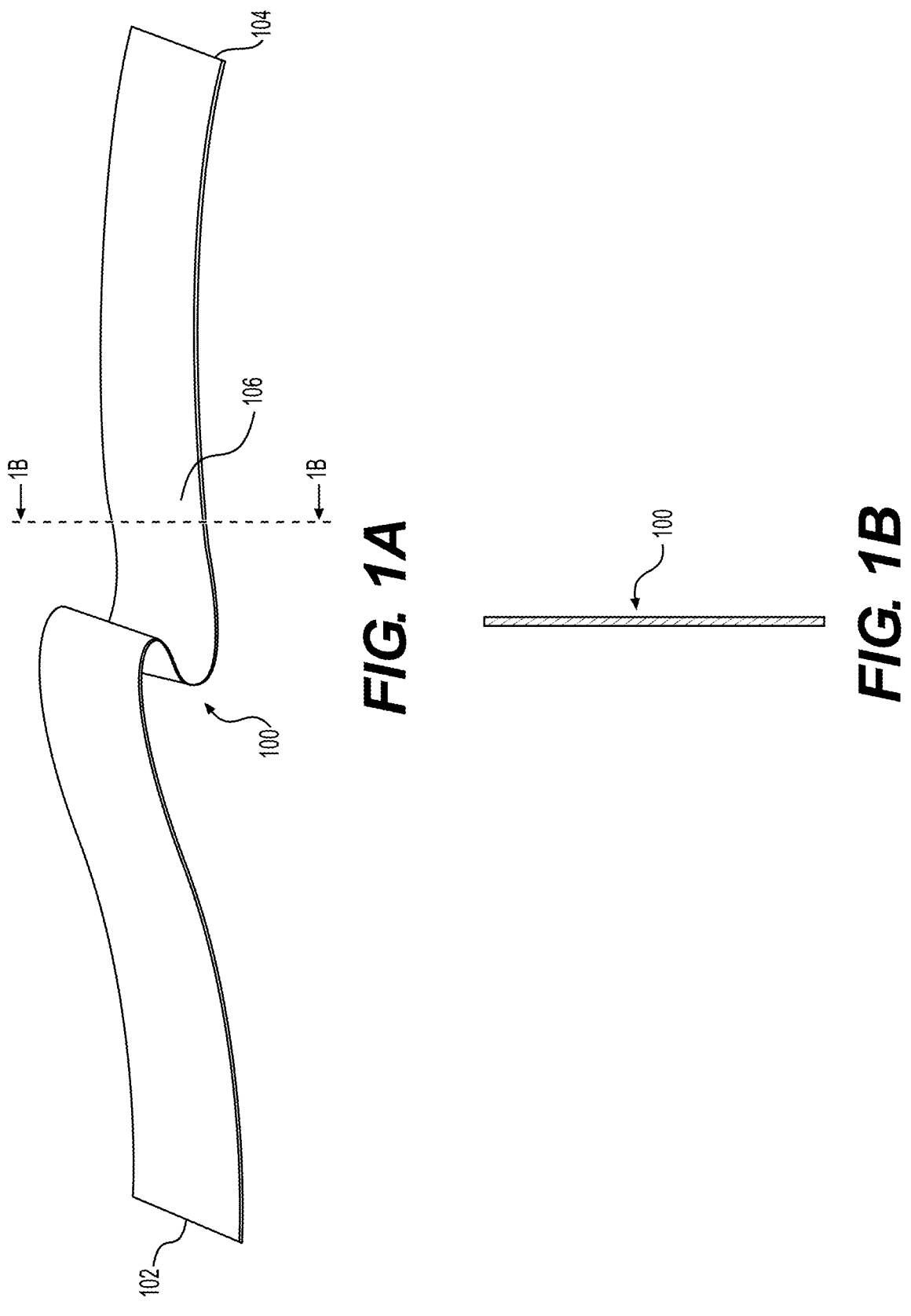
FIG. 1A shows an overall view for a first embodiment.
FIG. 1B shows a cross sectional view taken from line 1B-1B in FIG. 1A.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Synthetic slings have been available for implant procedures for many decades. The most common form of sling is constructed of polypropylene, which is typically comprised of woven or knit filaments. A polypropylene sling presents open structure which allows bacteria to penetrate. This can lead to post-operative infection. Although these devices have been implanted in many thousands of patients, there remain many post-implantation problems that have yet to be resolved. Most of these problems are clinically significant, and can end with surgical retrieval of the devices, which can lead to internal tissue damage.

One problem with these prior art polypropylene mesh slings is damage that can be caused upon surgical implant. Those skilled in the art will recognize that during surgery the polypropylene mesh sling is worked through bodily tissues, e.g., being pushed or pulled therethrough using needles or other devices. The edges of these prior art slings may be rough, and when passed through the body during surgical implant can create tissue damage, e.g., scar tissue, etc.

Any limited damage created upon implant of the polypropylene sling is not necessarily considered a bad thing, in that the damage causes an immediate inflammatory response, which ultimately helps incorporate the device structurally. But this damage can compromise tissues in undesirable ways also.

Another problem is that the polypropylene mesh degrades over time. This degradation can result in migration of sling segments or filaments, or even extrusion of the same. These obvious failures create harm, and often result in the need for removal of an already-implanted sling by a surgery far more complicated and potentially harmful than the initial implant procedure, and can leave behind massive scar tissue, as well as result in chronic pain moving forward.

Another problem is that of infection. The vulnerability of the polypropylene to infection is due in large part to the nature of the mesh material. Following implantation of a conventional polypropylene mesh sling, it is considered desirable that the surrounding tissues grow into the device. This ingrowth is seen as necessary to secure the polypropylene device in place. But this also makes the device extremely difficult to remove surgically, e.g., in the case of complications such as infection or structural degradation over time. Many times, surgery to remove the sling creates serious problems to the tissues on or around the implant.

The invention disclosed herein is a prosthetic medical sling made of a novel synthetic material, in embodiments, a relatively closed expanded Polytetrafluoroethylene structure. The inventive design of the medical device provides for a strong, supportive, biocompatible sling that resists bacterial invasion and disintegration.

The prosthetic sling embodiments disclosed herein overcome the aforementioned problems significantly.

More specifically, the embodiments described herein comprise a novel synthetic prosthetic medical sling that is biocompatible, resists bacterial infection, exhibits significant long-term strength to support tissues, does not promote massive scar tissue, and will not deteriorate over time. Further, the sling embodiments exhibit strength adequate for intended use, are supple and tissue compliant to minimize scar tissue formation, and are durable, as PTFE, a fluoropolymer, is known to be resistant to biodegradation.

Embodiments are comprised of a processed fluoropolymer, such as Polytetrafluoroethylene (PTFE). Embodiments disclosed in the figures herein incorporate expanded PTFE, or "ePTFE" which is formed by expansion under heat. An ePTFE article can be manufactured to have fibril lengths such that the article is a relatively closed structure to prevent the infiltration of bacteria, yet supple for tissue compliance, and adequately strong for its intended use as a tissue support device. And of course, as ePTFE, it is fully biocompatible and will not degrade.

The microporous structure of known ePTFE articles is characterized by a plurality of nodes that are connected together by a plurality of fibrils. The nodes are essentially solid PTFE, having a density of between about 2.0 grams to about 2.2 grams per cubic centimeter, whereas the density of the expanded material is less than about 2.0 grams per cubic centimeter. The shape, size, and orientation of the nodes and fibrils within the structure can be controlled by varying the expansion rate, expansion ratio, number of expansion axes, and other processing parameters to yield many different structures. It is also known that properties such as the expandability and microstructure of the expanded article vary with the molecular weight, particle size, and other physical characteristics of the PTFE resin.

An embodiment of the ePTFE article useable as an implant device (e.g., sling) is configured as a flat (roughly/substantially planar) elongated sheet embodiment as seen in FIGS. 1A and 1B. The body is made of a relatively closed structure, high strength, expanded fluoropolymer.

The embodiments above have shown no ingrowth as well as no bacterial penetration. Thus, they avoid the well-known infection problems existing in the polypropylene prior art devices. Additionally, because ingrowth is avoided, surgical removal is relatively easy to accomplish, if necessary, and leaves little, if any, scar tissue or other damage.

An embodiment 100 is shown in perspective in FIG. 1A. FIG. 1B shows a cross section taken at 1B-1B in FIG. 1A. The article 100 usable as a surgical supporting device includes a first end 102, a second end 104, and a substantially flat elongated body 106 (configured of a fluoropolymer in embodiments). The substantially flat elongated body 106 of the first version 100 is, in embodiments, comprised of multiaxially expanded PTFE that will ultimately reflect a node/fibril structure that can be made according to the practices discussed hereinafter.

The article is made, in embodiments, according to a process. More specifically, the article is produced by expanding PTFE in one dimension (i.e., uniaxially). Alternatively, the article can be expended in multiple dimensions (i.e., multiaxially). Beforehand, a resin paste can be mixed with an extrusion-aid such as mineral spirits, and then that paste can be compressed at relatively low pressures into a pre-extrusion form, e.g., as a pellet.

In embodiments, the material is extruded as a substantially flat article.

The PTFE article is then calendered while wet to a desired thickness. Because the article will be partially wet with mineral spirits, the process then moves on to a drying step where the lubricant is removed by subjecting it to a temperature slightly above the boiling point of the lubricant (e.g., about 150° C.), and far below the sintering or coalescing temperature of the polymer, generally at about 327° C. in embodiments.

Next, the article, in embodiments, is reheated at a temperature higher than the drying temperature, but below the melt temperature, e.g., above 240° C., in embodiments, or about 250° C. in more specific embodiments.

Next, the article is expanded in one or more dimensions. In embodiments where the article is expanded in a single dimension, or in other words "uniaxially expanded," the process will result in unidirectional elongated fibrils (which are substantially parallel) extending between nodes. These fibrils will have, in embodiments, lengths of about 0.5 microns to about 3 microns. In embodiments, the resulting pores will have approximate lengths of about 3 microns or less, and widths of about 1 microns or less. This pore sizes will not allow for ingrowth, and the article will have good strength. The extent of expansion of the PTFE makes the material softer, and here, that softness makes the ultimate device perform well.

Where the article is multiaxially expanded, the process may result in fibril lengths of between about 0.5 microns to about 3.0 microns. In embodiments, the resulting pore size is about less than or equal to 3.0 by 1.0 microns. Again here, these pore sizes will not allow for ingrowth, and the multiaxial expansion gives great strength. Also with the multiaxial arrangement, the extent of expansion of the PTFE makes the material softer, and here, that softness makes the ultimate device perform well.

Next, after expansion, the article is subjected to a final heat-treating step. In this step, the material is restrained in its expanded state and heated above the thermal transition temperature at about 350° C. to lock the structure in place.

Now expanded and locked, the ePTFE article is allowed to cool over a period of time at a lower temperature, e.g., at ambient.

Once the article has been processed as discussed above, the article can be presented for use along with existing implant systems and/or methods. The article can also be configured for use as a surgical implant.

The article can also be cut into desired sections or otherwise configured in ways making each section able to function as an individual sling.

As an optional additional step, an antimicrobial coating can be applied to the PTFE strip.

Figure 1C:
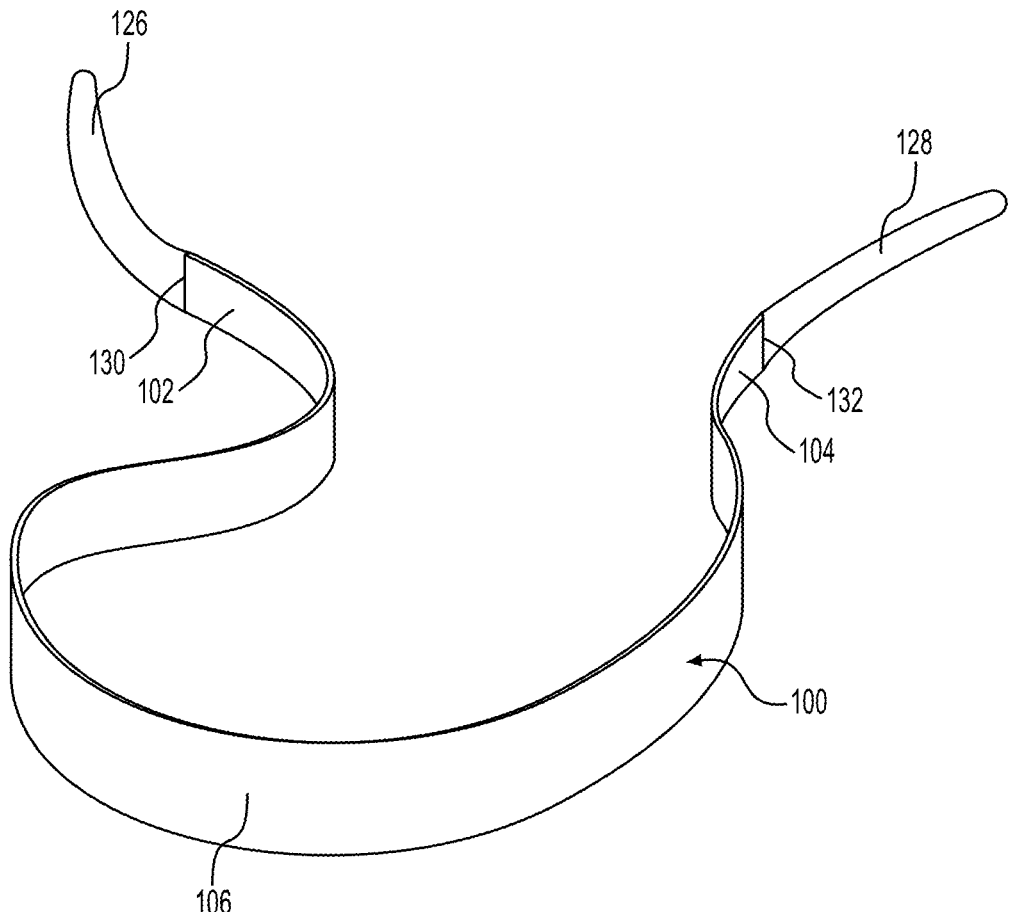
FIG. 1C depicts the article (shown in FIGS. 1A-B) as it might be attached to placement aids used for implant.

The ends of the cut strips (e.g., ends 102 and 104) can be configured for attachment to placement aids (e.g., needles) at each end of the article 100. FIG. 1C shows the PTFE article 100 attached to each of the placement aids 126 and 128.

The first and second ends 102 and 104 in FIG. 1C are shown being at connection locations 130 and 132. Those skilled in the art will recognize that numerous different sorts of ways that the connection aids 126 and 128 are connected to ends 102 and 104 exist in the art, e.g., the ends can be: (i) secured into clamps existing on each placement aids 126 and 128 (ii) ends 102 and 104 can be apertured for receipt of snaps on each placement aid (126 and 128); (iii) the ends of the article 100 can be knotted and then secured into V-shaped grooves formed into each aid (126 and 128); (iv) the placement aids 126, 128 can be attached using sutures; (v) attached using trocars; or (vi) other methods.

Example 1

In an embodiment, a resin paste was formed by blending 100% PTFE fine powder with an extrusion-aid (e.g., mineral spirits). The resulting resin paste was then formed into an extrusion pellet.

The PTFE article was extruded as a rectangular cross section, and calendered to a thinner cross section while wet. The ultimate thickness was about 0.60 mm after calendering.

After calendering, the lubricant was removed by subjecting the article to heat at a temperature of about 150° C. in order to dry the article (remove the mineral spirits).

With the lubricant now removed, the process moved on to an expansion step. In this embodiment of the expansion step, the article was then reheated at about 250° C. but below the melt temperature and expanded uniaxially. This expansion was made by securing each end of the article and expanding the article in a single direction longitudinally.

Following expansion, the material was restrained in its expanded state, and heated above the thermal transition temperature at about 350° C. to lock the structure in place.

Now expanded, the ePTFE article was allowed to cool over a period of time at a lower temperature, e.g., at ambient.

Figure 2:
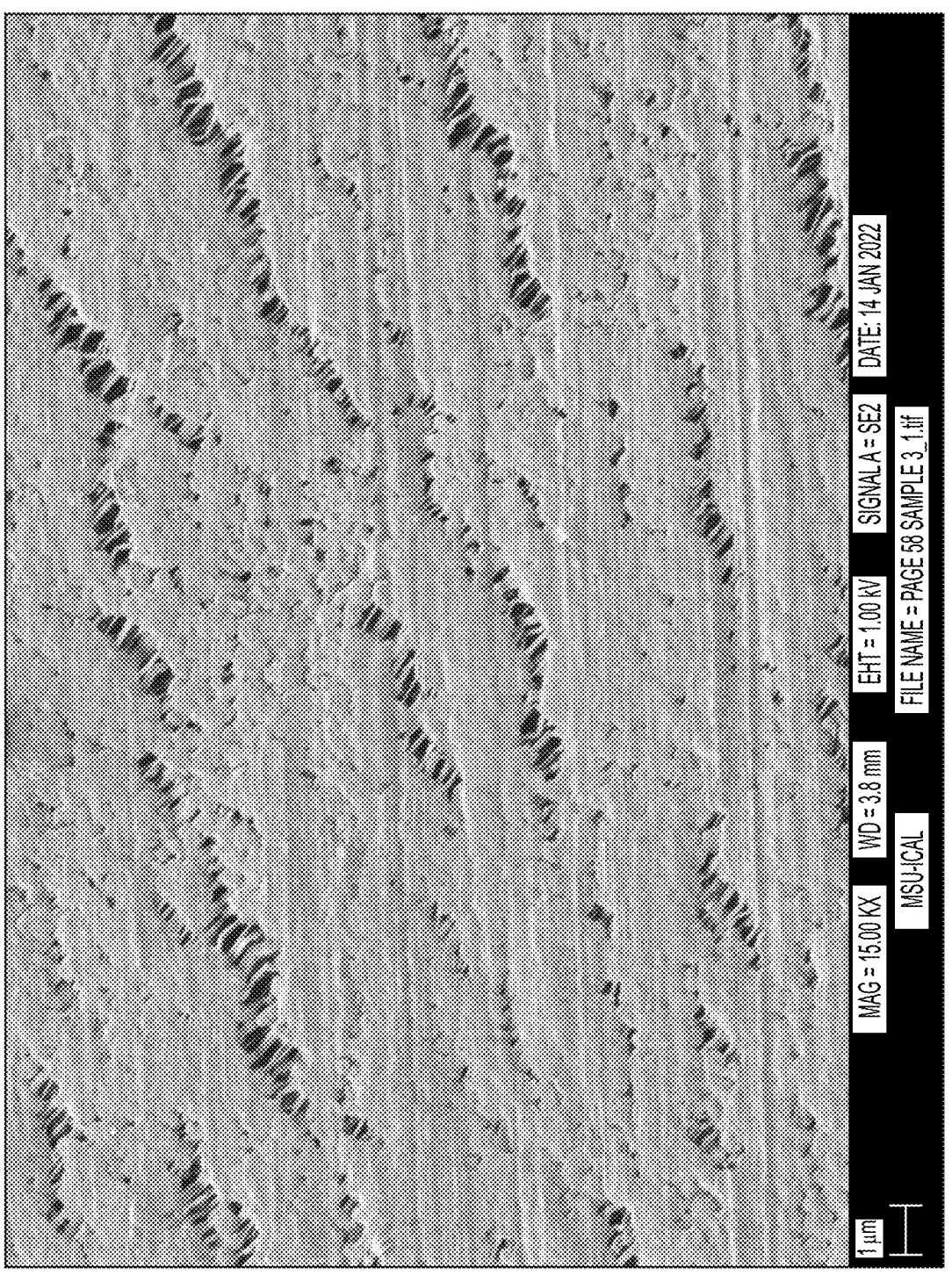
FIG. 2 is a micrograph taken of the material manufactured according to the process steps expressed herein where a single axis expansion is executed.

The extent of expansion of the PTFE was shown to give the material softness and other desired parameters discussed above making it ideal for use as a surgical sling. FIG. 2 is a micrograph taken of the material manufactured according to the processes discussed above. Referring to FIG. 2, it can be seen that the article has fibril lengths which are essentially less than about 3 micron. This size inhibits cells or bacteria from penetrating the material. Another noteworthy property is that the fibrils occupy limited space in the article, whereas the node sizes are relatively much larger. As can be seen from the FIG. 2 micrograph, more than about 80% of the area is comprised of solid nodes.

Example 2

In this embodiment, the same processes were followed as expressed above in Example 1 except that after calendering and lubricant removal, the article was multiaxially expanded. More specifically, the article was expanded in two dimensions, e.g., longitudinally and laterally (in directions offset by 90 degrees).

Figure 3:
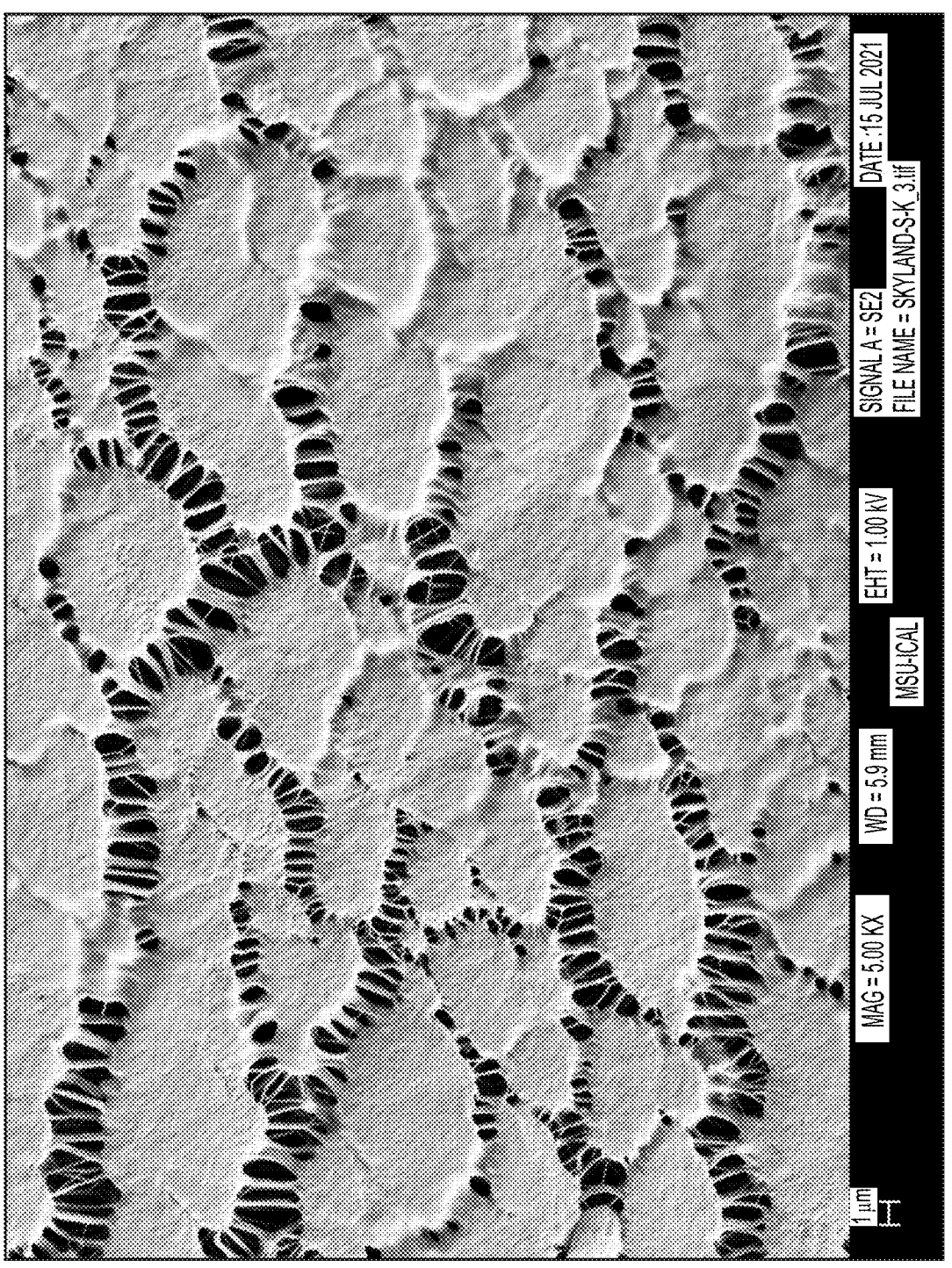
FIG. 3 a micrograph taken of the material manufactured according to the process steps expressed herein where a multiaxial expansion is executed.

Again here, the expansion of the PTFE was shown to give the material softness and other desired parameters making it ideal for use as a surgical sling. FIG. 3 is a micrograph taken of the material manufactured according to the processes discussed in this example. Referring to the figure, it can be seen that the article has a fibril lengths which are, generally speaking, range from about 0.5 micron to about 1.0 micron. The uniaxial expansion creates elongated pores between the nodes which have widths that range in size, but are always lower than 2 micron. This size inhibits cells or bacteria from penetrating the material. Again here, fibrils occupy limited space in the article, and the node sizes are relatively larger. As can be seen from the FIG. 3 micrograph, more than about 80% of the area is comprised of solid nodes.

Although the descriptions above relate to the use of ePTFE articles as prosthetic slings to stabilize a patient's urethra or bladder as described above, they could also be useful in providing support for other organs. Additionally, multiple strips could be used together for certain applications. Further, the articles could be used for the support of rectal muscles in other applications.

Features described above as well as those claimed below may be combined in various ways without departing from the scope hereof. The following examples illustrate some possible, non-limiting combinations:

(A1) A surgical implant including: an elongated body configured to support a body tissue, the elongated body including and a first end and a second end, the elongated body formed of a biocompatible, bacteria-resistant fluoropolymer material, the biocompatible, bacteria-resistant fluoropolymer material includes a plurality of nodes and a plurality of fibrils, the plurality of fibrils interconnecting the plurality of nodes.

(A2) For the surgical implant denoted as (A1), the biocompatible, bacteria-resistant fluoropolymer material includes Polytetrafluoroethylene (PTFE).

(A3) For the surgical implant denoted as (A1) or (A2), the biocompatible, bacteria-resistant fluoropolymer material includes expanded PTFE (ePTFE).

(A4) For the surgical implant denoted as any of (A1) through (A3), the elongated body is substantially planar.

(A5) For the surgical implant denoted as any of (A1) through (A4), the surgical implant is substantially microporous.

(A6) For the surgical implant denoted as any of (A1) through (A5), the elongated body is multiaxially expanded such that the plurality of fibrils radiate between the plurality of nodes to define a plurality of pores.

(A7) For the surgical implant denoted as any of (A1) through (A6), the plurality of fibrils are about 0.5 to about 3 microns in length.

(A8) For the surgical implant denoted as any of (A1) through (A7), the plurality of pores defined between the plurality of nodes and fibrils are less than or equal to 2 by 1 microns in size.

(A9) For the surgical implant denoted as any of (A1) through (A8), the elongated body is uniaxially expanded such that the plurality of fibrils extend substantially longitudinally between the plurality of nodes to define a plurality of elongated pores.

(A10) For the surgical implant denoted as any of (A1) through (A9), the plurality of fibrils are about 0.5 to about 3.0 microns in length.

(A11) For the surgical implant denoted as any of (A1) through (A10), the plurality of pores defined between the plurality of nodes and the plurality of fibrils have widths which are less than about 3 microns.

(A12) For the surgical implant denoted as any of (A1) through (A11), the elongated body has a thickness of about 0.60 mm.

(A13) For the surgical implant denoted as any of (A1) through (A12), the surgical implant is configured for use as a pubovaginal sling.

(A14) For the surgical implant denoted as any of (A1) through (A13), the first end is configured to receive a first surgical placement aid, and the second end is configured to receive a second surgical placement aid.

(A15) For the surgical implant denoted as any of (A1) through (A14), the biocompatible, bacteria-resistant fluoropolymer material includes a microporous structure which is relatively closed to ingrowth and bacterial penetration.

(B1) A method for producing a supportive surgical implant device, the method including: mixing a PTFE resin paste with an extrusion aid; configuring the PTFE resin paste and the extrusion aid into a pre-extrusion form; calendaring the pre-extrusion form to make a PTFE article; drying the extrusion aid from the PTFE article; reheating the PTFE article at a temperature higher than a drying temperature used in the drying step, but lower than a melt temperature of the PTFE article; expanding the PTFE article to create a node/fibril structure; restraining the PTFE article in an expanded state and heating the PTFE article to a temperature above a thermal transition temperature for the PTFE article to lock the node/fibril structure in place; allowing the PTFE article to cool; and configuring the PTFE article for use as the supportive surgical implant device.

(B2) For the method denoted as (B1), including: forming the PTFE article into a sheet; and causing at least a portion of the sheet to have an elongated body and two ends.

(B3) For the method denoted as (B1) or (B2), including: configuring the ends of the at least a portion of the sheet to attach to one or more surgical placement aids.

(B4) For the method denoted as any of (B1) through (B3), the expanding step is a substantially unidirectional expansion resulting in a plurality of elongated fibrils, each fibril in the plurality being substantially parallel relative to the others.

(B5) For the method denoted as any of (B1) through (B4), the expanding step is a multiaxial expansion resulting in a plurality of fibrils which radiate between a plurality of nodes.

Many different arrangements of the various components depicted, as well as components not shown, are possible without departing from the spirit and scope of what is claimed herein. Embodiments have been described with the intent to be illustrative rather than restrictive. Alternative embodiments will become apparent to those skilled in the art that do not depart from what is disclosed. A skilled artisan may develop alternative means of implementing the afore-mentioned improvements without departing from what is claimed.

It will be understood that certain features and sub-com-binations are of utility and may be employed without reference to other features and sub-combinations and are contemplated within the scope of the claims. Not all steps listed in the various figures need be carried out in the specific order described.

What is claimed is:

1. A surgical implant comprising:
an elongated flat implant body having first and second ends, the implant body being configured to support a body tissue, the body formed of a biocompatible, bacteria-resistant fluoropolymer material,
wherein the biocompatible, bacteria-resistant fluoropoly-mer material comprises a plurality of nodes and a plurality of fibrils, wherein the implant body is multi-axially expanded such that the plurality of fibrils radiate between the plurality of nodes to define a plurality of pores, each of the plurality of pores each having a length and a width, a smallest of the length or width being about equal to or less than about 2 micron, wherein more than about 80% of the implant body is comprised of solid nodes, and
wherein the biocompatible, bacteria-resistant fluoropoly-mer material comprises a microporous structure which is closed to ingrowth and bacterial penetration.

2. The surgical implant of claim 1, wherein the biocom-patible, bacteria-resistant fluoropolymer material comprises Polytetrafluoroethylene (PTFE).

3. The surgical implant of claim 2, wherein the biocom-patible, bacteria-resistant fluoropolymer material comprises expanded PTFE (ePTFE).

4. The surgical implant of claim 1, wherein the surgical implant is substantially microporous.

5. The surgical implant of claim 1, wherein the plurality of fibrils are about 0.5 to about 3 microns in length.

6. The surgical implant of claim 1, wherein the plurality of pores defined between the plurality of nodes and fibrils are less than or equal to 2 by 1 microns in size.

7. The surgical implant of claim 1, wherein the implant body has a thickness of about 0.60 mm.

8. The surgical implant of claim 1, wherein the surgical implant is configured for use as a pubovaginal sling.

9. The surgical implant of claim 8, wherein the first end is configured to receive a first surgical placement aid, and the second end is configured to receive a second surgical place-ment aid.

10. The surgical implant of claim 1, wherein the plurality of pores are about 0.5 microns to about 1.0 microns.

11. The surgical implant of claim 1, wherein the implant body is configured for organ engagement.

12. The surgical implant of claim 1, wherein the implant body is configured for the receipt of surgical placement aids.

13. An expanded PTFE tissue-engaging surgical implant comprising
a body formed of expanded PTFE, the body having:
a microporous structure including a plurality of nodes and a plurality of multiaxially-radiating fibrils, the plurality of multiaxially-radiating fibrils radiate between the plurality of nodes to establish a plurality of pores, each of the plurality of pores having sizes which are less than or equal to about 2 microns, wherein more than about 80% of the body is comprised of solid nodes, and
the microporous structure being closed to ingrowth and bacterial penetration.

14. The expanded PTFE tissue-engaging surgical implant of claim 13, wherein the plurality of multiaxially-radiating fibrils have lengths from about 0.5 microns to about 1.0 microns.

15. The expanded PTFE tissue-engaging surgical implant of claim 13, having smooth edges which prevent damage upon implant.

* * * * *